United States Patent [19]

Anders, Jr.

[11] Patent Number: 4,989,591
[45] Date of Patent: Feb. 5, 1991

[54] PRONE POSITION ORTHOPEDIC APPLIANCE FOR ALIGNING THE SPINE AND THE FEMORAE

[76] Inventor: Frank Anders, Jr., P.O. Box 630, Ville Platte, La. 70586

[21] Appl. No.: 307,611

[22] Filed: Feb. 8, 1989

[51] Int. Cl.$^5$ .............................................. A61F 5/32
[52] U.S. Cl. ......................................... 128/69; 5/431; 128/78
[58] Field of Search ............... 128/78, 69; 5/436, 431, 5/443

[56] References Cited

U.S. PATENT DOCUMENTS

| | | | |
|---|---|---|---|
| 1,924,640 | 8/1933 | Draves | 128/78 X |
| 2,552,475 | 5/1981 | Austlid | 128/78 |
| 2,617,412 | 11/1952 | Steinberger | 128/78 |
| 2,733,712 | 2/1956 | Wuesthoff | 128/78 |
| 2,813,526 | 11/1957 | Beebe | 128/78 |
| 2,871,850 | 2/1959 | Peckham | 128/78 |
| 3,052,236 | 9/1962 | Schrieber | 128/78 |
| 3,307,535 | 3/1967 | Locke | 128/78 |
| 3,489,142 | 1/1970 | Golay | 128/74 |
| 3,605,731 | 9/1971 | Tigges | 128/24 R |
| 4,118,813 | 10/1978 | Armstrong | 5/337 |
| 4,135,503 | 1/1979 | Romano | 128/78 |
| 4,175,553 | 11/1979 | Rosenberg | 128/78 |
| 4,178,923 | 12/1979 | Curlee | 128/78 |
| 4,473,913 | 10/1984 | Ylvisaker | 5/435 |
| 4,616,639 | 10/1986 | Huber | 128/99.1 |
| 4,627,109 | 12/1986 | Carabelli et al. | 128/78 X |
| 4,702,235 | 10/1987 | Hong | 128/78 |
| 4,756,090 | 7/1988 | Pedrow | 128/78 X |
| 4,796,315 | 1/1989 | Crew | 128/78 X |

Primary Examiner—David A. Wiecking
Assistant Examiner—Moshe I. Cohen
Attorney, Agent, or Firm—Banner, Birch, McKie and Beckett

[57] ABSTRACT

An orthopedic appliance and method for changing the angular relationship of an individual's longitudinal axis of the lower lumbar spine to a longitudinal axis of the femorae which includes a support device having a lower surface to be disposed along a resting surface. The support device also includes an upper surface having first and second surface portions which are angularly disposed relative to one another. The first and second surface portions are to be applied against a front portion of an individual near the individual's lower lumbar spine and femorae. The angular relationship between the first and second upper surface portions recreates in an individual an angle between the longitudinal axis of the lower lumbar spine and the longitudinal axis of the femorae which is approximately equal to the angular relationship between these longitudinal axes while an individual is standing. The prone position recreated angle between the longitudinal axis of the lower lumbar spine and the longitudinal axis of the femorae will range approximately between 120° and 140° as measured about the support device side of each of these longitudinal axes. Preferably this angle will equal approximately 130° and the angles formed by planes from two upper surface portins in relationship to a plane from the lower surface of the support device will be approximately 25° each.

29 Claims, 3 Drawing Sheets

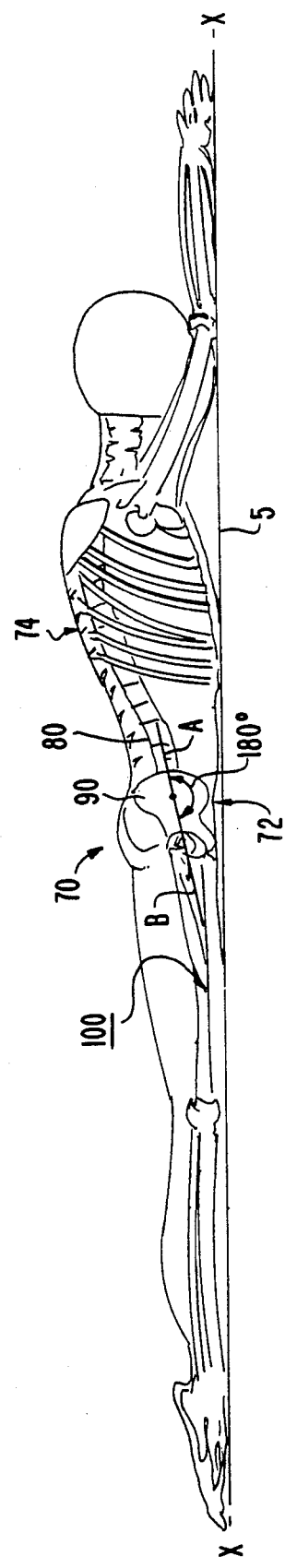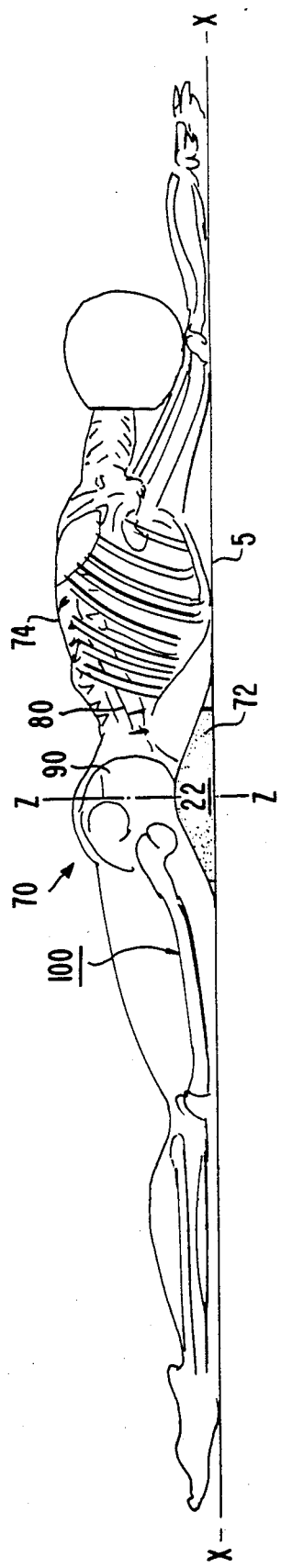

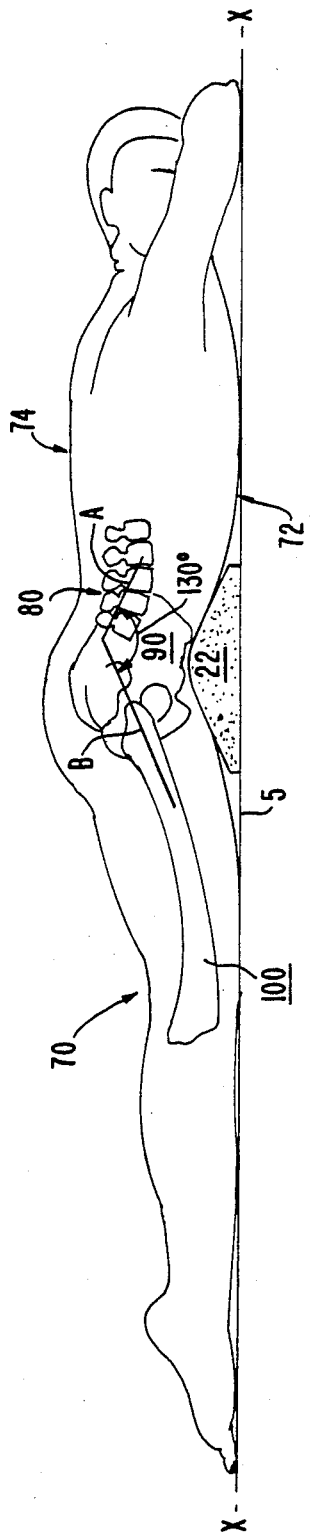
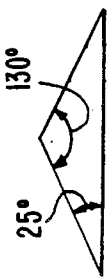
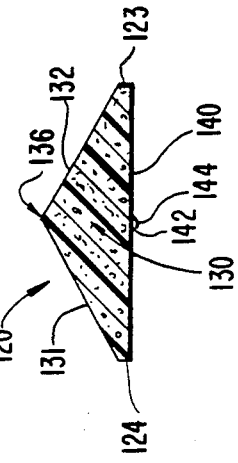
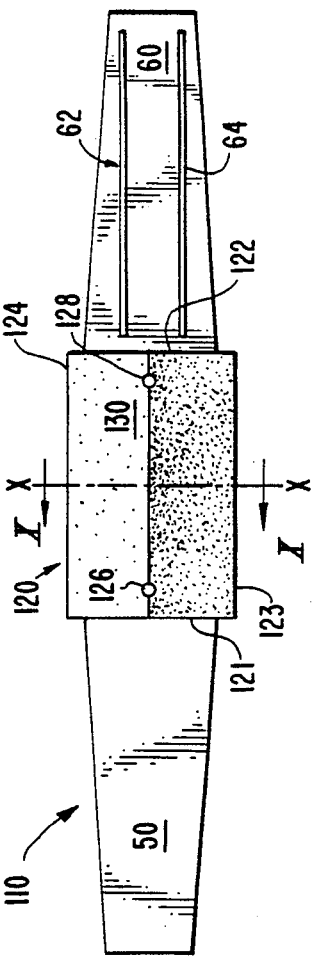

PRONE POSITION ORTHOPEDIC APPLIANCE FOR ALIGNING THE SPINE AND THE FEMORAE

I. BACKGROUND OF THE INVENTION

This invention relates to an orthopedic appliance and a method for realigning the spine and the femorae when the user is in the prone position. More specifically, this invention relates to an orthopedic appliance having a support device which can recreate the angle made while an individual is standing between a longitudinal axis of the lower lumbar spine and the longitudinal axis of the femorae when the user is lying in the downward facing or prone position.

Illustrated in FIG. 1 is a human body 70, having front side 72 and back side 74, lying lengthwise on a resting surface, bed or the like 5 in a prone position along a longitudinal axis X—X. The internal body structures shown include the sacrum 90, the portion of the spinal column situated along the lowermost five discs in the part of the back between the lowermost ribs and the sacrum and called the lumbar spine 80 and the bones extending from the hip to the knee called the femorae 100. The longitudinal axis of the lower lumbar spine A is defined as the line running through the center portion of the last two discs of the lumbar portion 80 of the spinal column. The longitudinal axis of the femorae B is defined as the line running through the center of the upper slightly curved portions of the femorae 100. The location of the abdominal area containing the stomach, intestines, liver and other visceral organs and the bladder region are known to those in the orthopedic art and, thus, not shown.

The Applicant has concluded from lateral projection X-ray tests that when a sizable percentage of individuals are standing or laying on their back on a firm, substantially planar resting surface, the longitudinal axis of their lower lumbar spine in relation to the longitudinal axis of their femorae is approximately within a range of 120° to 140°, as measured about the sides of these axes facing a front side of the individuals. The largest concentration of these individuals have their lower lumbar spine to femorae longitudinal axes form approximately a 130° angle to each other when the individuals are standing or lying on their backs.

As seen in FIG. 1, when an individual 70 is lying in a prone position, even with a relatively good sleeping posture and a firm, substantially planar resting surface 5, a deforming force is caused between the lower lumbar spine 80 and the femorae 100. This deforming force is mainly caused by the weight of the pelvis. This deforming force causes the angular relationship, as viewed from a front side 72 of the individual 70, between the longitudinal axis of the lower lumbar spine A and the longitudinal axis of the femorae B to increase or open out to approximately a parallel or 180° relationship between these two axes as shown in FIG. 1. This change in the femorae and the lower lumbar spine axes position between the standing and the prone position can cause excessive compressive forces on the lower region of the back. Of most concern is the pressure these forces place on the apophyseal joints in the region of the lumbosacral junction. This change in the axes relationship, therefore, can lead to considerable pain of the lower back.

There have been proposed various orthopedic appliances which are directed to maintaining and correcting posture. These appliances, when directed to prone position posture, teach pads of a general rounded structure on the front side of an individual.

U.S. Pat. No. 2,617,412 to Steinberger discloses a pad 7 on the abdomen which may be of a thickness to support the spine in a proper manner while the individual, while sleeping, occupies a prone position in which the size, shape, position and thickness of the pad will depend on the size of the wearer and the corrective measures sought. In Steinberger, the pads, formed of any suitable soft or yieldable substance, possess their maximum thickness in the centers thereof and taper to substantially a feather edge at their outer margins, so as to provide comfort.

U.S. Pat. No. 4,616,639 to Huber discloses an elasticized orthopedic-type belt for obtaining correct anatomical position (i.e., slight lordosis) of the lumbosacral spine while lying prone. Included in Huber are resilient foam anterior pads 28 and 30 to provide support under the anterior superior iliac spines when the wearer is lying prone to prevent the pelvis from rolling forward into an anterior pelvic tilt.

U.S. Pat. No. 2,813,526 to Beebe discloses an abdominal pad 28 to overcome sacroiliac slip, i.e., excessive rearward movement about the sacroiliac joint, when an individual is walking. The abdominal pad of Beebe has a lower section with an inward curve.

None of the above mentioned references apparently teach the importance of a biomechanical supporting appliance pad with surfaces at such angles to realign the lower lumbar spine in relation to the femorae to offset the change in relationship of the axes during normal prone sleeping position. Therefore, it is considered an improvement to have an orthopedic appliance to recreate the angle made, while standing, between a longitudinal axis of the lower lumbar spine and a longitudinal axis of the femorae when the user is lying in a prone position.

II. SUMMARY OF THE INVENTION

It is an object of this invention to substantially relieve lower back pain known to be experienced by many people when lying in the prone position.

It is another object to provide greater relief for lower back pain when an individual is lying in a prone position than is normally gained from generally round shaped pads.

It is still another object to recreate the normal standing angle between the lower lumbar spine and the femorae while an individual is in the prone position.

The present invention includes an orthopedic appliance for changing the angular relationship of an individual's longitudinal axis of the lower lumbar spine to a longitudinal axis of the femorae when an individual is in a prone position. This appliance includes a support device having a lower surface to be disposed along a resting surface and an upper surface disposed above the lower surface. The upper surface includes first and second surface portions angularly disposed relative to one another. The first surface portion is to be applied against a front portion of an individual approximately near the lumbar spine of an individual when the individual is lying in a prone position. The second surface portion is to be applied against a front portion of an individual near the femorae. In addition, the angular relationship between the first and second upper surface portions recreates between the longitudinal axis of the lower lumbar spine and the longitudinal axis of the femorae an angle approximately equal to the angular relationship between these longitudinal axes while an individual is standing.

The present invention also includes a method for changing the angular relationship of an individual's longitudinal axis of the femorae when an individual is lying in a prone position. This method includes the steps of placing a lower surface of the support device on a resting surface and positioning an upper surface of the support device against a front portion of an individual. The upper surface having first and second surface portions angularly disposed relative to one another. This method also includes the steps of applying the first upper surface portion against a front portion of an individual near the lumbar spine of an individual, and applying the second upper surface portion against a front portion of an individual near the femorae of an individual. The angular relationship between the first and second upper surface portions then recreates in an individual an angle between the longitudinal axis of the lower lumbar spine and the longitudinal axis of the femorae which is approximately equal to the angular relationship between these longitudinal axes when an individual is standing.

The orthopedic appliance includes the above mentioned support device and it can also include straps or the like for releasably securing the pad on an individual. The support device has a longitudinal axis along which an individual would lay in a prone position. A support device housing can have compressible foam-like material disposed within it. The housing also can have first and second side surfaces which extend approximately parallel to a longitudinal axis of the support device, third and fourth side surfaces which extend approximately perpendicular to a longitudinal axis of the support device, and a lower surface to be disposed along a resting surface. Further, the housing includes an upper surface against which an individual would lay in a prone position along a longitudinal axis of the support device. The upper surface can have a center portion near a center point of a longitudinal axis of the support device and a plurality of upper surface portions each of which lie in a separate plane. Each upper surface portion plane extends downward from the center portion of the upper surface of the support device in an opposite direction from a center portion of the upper surface along a longitudinal axis of the support device. Each of the pair of planes are disposed at an angle approximately between 20° and 30°, while preferably about 25°, to a plane extending longitudinally from the lower surface portion. The pair of upper surface planes can also intersect each other at a point approximately near a center portion of the upper surface at an interior facing angle of the support device of approximately 120° to 140°, while preferably about 130°.

The advantages of this invention are at least two-fold. Since many individuals have lower lumbar pain in the prone position, by recreating the relationship while standing between the femorae and the lower lumbar spine this orthopedic appliance can substantially reduce the prone position lower back pain. The advantageous structure is also a low-cost design.

Other objects, features, and characteristics of the present invention, as well as the methods, operation and functions of the related elements of the structure, the combination of parts and economies of manufacture, will become apparent upon consideration of the following description and the appended claims with reference to the accompanying drawings, all of which form a part of the specification, wherein like reference numerals designate corresponding parts in the various figures.

III. BRIEF DESCRIPTION OF THE DRAWINGS

A more complete appreciation of the invention and many attendant advantages thereof will be readily obtained as the same becomes better understood by reference to the following detailed description when considered in connection with the accompanying in which:

FIG. 1 is a side view of a human body showing an individual in a prone position against a resting surface;

Figure 2:
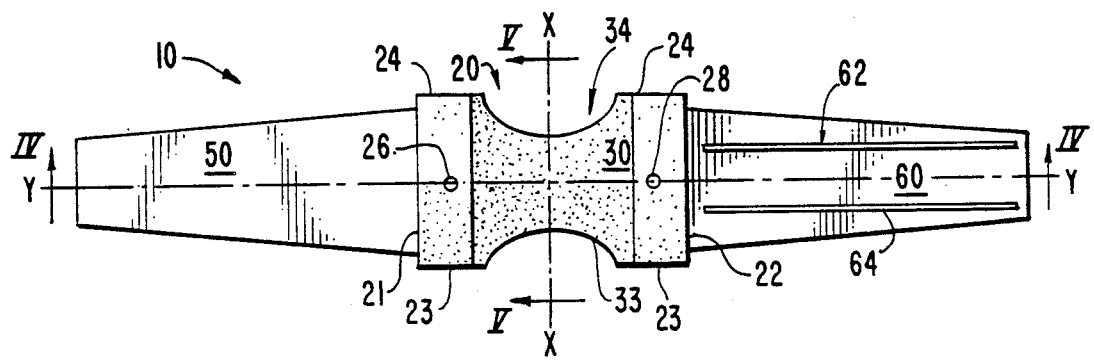
FIG. 2 is a plan view of a preferred embodiment of the support device and straps of the orthopedic appliance.

FIG. 6 illustrates the preferred superior angular relationship along an axis parallel to the X—X axis of FIG. 2 between intersecting planes extending from upper surface portions of the orthopedic appliance support device and the preferred inferior angular relationship along this same axis between a plane extending from the lower surface of the support device and the planes of the upper surface portions of the support device;

FIG. 7 is the same side view of the human body in a prone position as in FIG. 1 with the support device of the orthopedic appearance device of FIGS. 2-5 disposed in position on the front side of an individual;

FIG. 8 is similar to FIG. 7 with the addition of lines illustrating the longitudinal axis of the lower lumbar spine, the longitudinal axis of the femorae and the preferred angular relationship obtained between these two axes when the support device of the orthopedic appliance device is in position on the front side of an individual;

FIG. 9 is a plan view of a modified embodiment of the orthopedic appliance of FIG. 2; and FIG. 10 is a sectional view along line X—X of FIG. 9.

IV. DETAILED DESCRIPTION OF THE PREFERRED EMBODIMENTS

Figure 4:
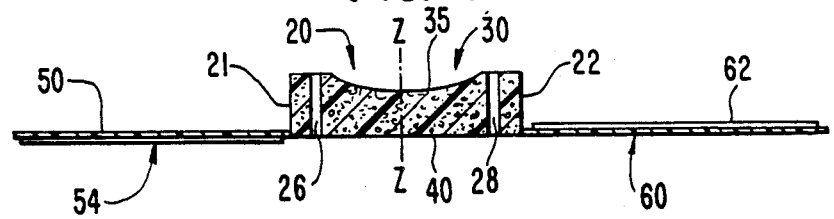
FIG. 4 is a sectional view along line IV—IV of FIG. 2 which is also the Y—Y axis of FIG. 2.
Figure 5:
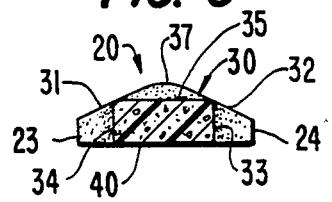
FIG. 5 is a sectional view along line V—V of FIG. 2 which is also the X—X axis of FIG. 2.

FIGS. 2-5 illustrates a preferred embodiment of the orthopedic appliance device 10. The device includes a support device 20 and a retaining strap or, in these illustrations, retaining straps 50 and 60. The support device 20 is preferably a pad, cushion or the like having a housing filled with compressible foam-like material as seen in FIGS. 4 and 5. The support device 20 lies along a longitudinal axis X—X. It is along this same longitudinal axis X—X which an individual will lay in a prone position.

The support device 20 of this embodiment includes an upper surface 30, a lower surface 40 and side surfaces 21 and 22 which are approximately parallel to a longitudinal axis of the support device. The lower surface is designed to be disposed along a resting surface, bed or the like 5. This lower surface can be lying directly against the resting surface or, alternatively, the retaining strap or straps can be lying against the resting surface with the support device lying against and connected to the strap while also being disposed along the resting surface. Side surfaces 23 and 24 are approximately perpendicular to a longitudinal axis of the support device and approximately perpendicular to the side surfaces 21 and 22. Elongated apertures 26 and 28 extend through and between the upper surface 30 and lower surface 40 of the pad at positions along the latitudinal axis of the appliance Y—Y.

Figure 3:
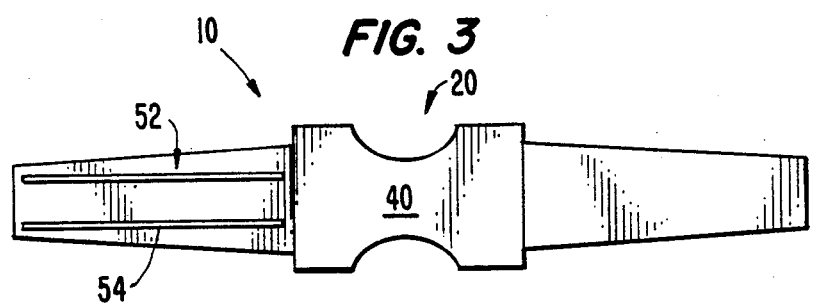
FIG. 3 is a bottom view of the orthopedic appliance of FIG. 2.

As illustrated in FIGS. 2-4, the retaining straps 50 and 60 are attached near the lower surface 40 of the support device 20. Hook and loop fasteners such as VELCRO strips 62 and 64 on a top side of strap 60 are to be engaged with VELCRO strips 52 and 54 on a bottom surface of strap 50 on the back side of an individual. This engagement along the individual's back will retain the support device 20 in its operative position despite movement while the individual is resting or sleeping.

As illustrated in the sectional view of FIG. 5, along a longitudinal axis of FIG. 2 the support device upper surface 30 can be divided into two substantially planar upper surface portions 31 and 32 meeting at portion 37. As derived from FIGS. 2 and 4, a portion 37 is disposed along the latitudinal axis Y—Y and is at the highest portion (on a Z—Z axis) of the upper surface of the support device.

FIG. 6 shows the relationship of planes extending along the upper surface portions 31 and 32 and the lower surface 40 along the same view as in FIG. 5 and along a longitudinal axis of FIG. 2. The planes extending along the upper surface portions 31 and 32 preferably intersect each other at a downward or interior upper device facing angle of 130°. These upper surface planes then each preferably intersect the lower surface 40 plane at substantially equal angles of 25°. The intersection of the planes extending from upper surface portions 31 and 32 is near the center portion 37 of the support device 20, but not necessarily at a point on the support device. For example, the center portion 37 could be somewhat round at the top and the intersection of the upper surface portion planes would then not likely be at a point on the support device.

FIGS. 7 and 8 illustrate the effect the orthopedic appliance support device has on the lumbar spine 80 and the femorae 100 of an individual 70 lying in a prone position along a longitudinal axis of the pad and disposed on a resting surface 5. As more clearly shown in FIG. 8, with the preferred orthopedic appliance support device on a resting surface 5 in a position on the front side 72 of an individual 70 near the sacrum 90, the longitudinal axis of the lower lumbar spine A will be approximately 130° to the longitudinal axis of the femorae B as measured about an angle facing the support device or the front side 72 of the individual 70.

In comparison to FIG. 1, with the preferred support device 20, the interior or front side facing angular relationship of the longitudinal axis of the lower lumbar spine A to the longitudinal axis of the femorae B can be reduced from about 180° to about 130°. The reason this change in angular relationship occurs is because the support device, when placed upon an approximately planar resting surface 5, has upper surfaces portions 31 and 32 at approximately 120°-140° and preferably about 130° to each other and planes extending from these upper surfaces each rise from the lower surface 40 of the pad at approximately 20°-30° and preferably about 25° to the lower surface plane. One upper surface portion, for example 31, pushes a front portion of the body near the lumbar spine or an upper portion of the sacrum 90 upwards approximately 20°-30° (preferably about 25°) relative to its prior position so that the longitudinal axis of the lumbar spine A moves downward and towards the pelvis area. The other top surface portion 32 pushes a front portion of the body near the femorae or a lower portion of the sacrum 90 upwards approximately 20°-30° (preferably about 25°) relative to its prior position so that the longitudinal axis of the femorae B moves downward and towards the sacrum area. The longitudinal axes, therefore, of the lower lumbar spine and the femorae each move towards each other approximately 20°-30° (preferably about 25°) relative to the front portion of the body. Consequently, their longitudinal axes, about an angle facing the front side of the body, move to approximately 120°-140° (preferably about 130°) apart.

The orthopedic appliance, therefore, recreates when an individual is in the prone position, the angle made while an individual is standing between the longitudinal axis of the lower lumbar spine A and the longitudinal axis of the femur B. With this angle recreating orthopedic appliance support device an individual who is relatively pain free when standing or lying on his or her back but experiences lower back pain in a prone position, despite good sleeping posture and laying on a firm, substantially planar resting surface, can reduce the stresses and pressure on the apophyseal joints in the region of the lumbosacral junction, the lumbar discs, or the muscles to relieve pain. Instead of possible relief with generally round shaped pads, with the support device of the present invention, the standing angle is recreated and freedom from pain when standing will more than likely assure freedom from pain when in the prone position. Using this support device to recreate an angle of approximately 120° to 140° between the two longitudinal axes should be able to achieve the above improved results in a sizable percentage of the population.

As seen from the top view of FIG. 2 and the bottom view of FIG. 3, the support device is preferably of a rectangular shape with the length of side surfaces 23 and 24 being greater than the length of side surfaces 21 and 22. Preferably the length of the side surfaces 23 and 24 are 6-8 inches long where the length of the side surfaces 21 and 22 are 4-6 inches long. Consequently, the support device preferably stretches a greater distance latitudinally across the front of the body rather than longitudinally or lengthwise along the front of the body. With the support device substantially rectangular to stretch further latitudinally across the body than longitudinally along the body, the support device can stretch out under the points of the hips while contact with the bladder region and abdominal area is reduced.

Also illustrated in FIGS. 2-5 are semi-circular inwardly facing side surface portions 33 and 34 which lie along side surfaces 23 and 24. These semi-circular inward directed side portions 33 and 34 are centered along a longitudinal axis X—X of the surface device. They are designed to further prevent the support device upper surfaces from exerting upward or compressive force pressure on the abdominal and bladder areas by reducing to a minimum or totally eliminating contact of the abdominal area and bladder region with the support device. The portion 34 facing forward, or towards a head of an individual, defines an open area or aperture to prevent substantial pressure from being exerted on the abdominal area and thus, the stomach, intestines, liver and other visceral organs. The portion 33 facing rearward, or towards the feet of an individual, prevents substantial pressure from being exerted on the bladder region. Consequently, while in the prone position, the bladder and abdomen are prevented from substantial pressure from the bones making up the points of the hips or the sacrum are raised, and the desired standing angle between the longitudinal axes of the femur B and the lower lumbar spine A is obtained.

Also illustrated in FIGS. 4 and 5 is a concave portion 35 which can be positioned along the center of the support device about the X—X axis so that the points of the hips can contact the upper surface portions 31 and 32 of the device, yet the front side of an individual between the points of the hips will be relieved from substantial pressure from the support device. In other words, the illustrated upper surface comprises upper surface portions 31 and 32 with or without the added concave portion 35.

The support device 20 preferably includeds a housing which can be vinyl. The housing of the support device is disposed around cellular or non-cellular foam or fibrous materials.

The preferred closed cell foam can uniformly compress so that the support device can be maunufactured with the same angle relationships as desired when in compressed state. For example, the support device can be manufactured with planes extending from the upper surface portions at approximately 120°-140° to each other about an interior support device angle and with the plane extending from the bottom surface approximately 20°-30° to each of the upper surface planes.

An alternative embodiment orthopedic appliance support device 120 is illustrated in FIGS. 9 and 10. The last two digits of the three digit numbers of FIGS. 9 and 10 correspond to their similar two digit elements in FIGS. 2-8. In FIGS. 9 and 10, the upper surface portions 131 and 132 actually meet in an apex 136 defining the common point of a preferred 130° interior facing angle. This apex is desirable if one wants the uplifting effect along the complete upper surface. Note, planes of the upper surface portions 131 and 132 intersect as this apex 136 on the support device.

The preferred foam or fibrous material of this embodiment has a controlled rigidity, but no semi-circular inwardly facing side surface portions. When a individual is in a prone position along a longitudinal axis of the support device 120, this device is sufficiently rigid for the top surface of the support device to have a cross-sectional angle along a longitudinal axis of the support device which substantially equals the angle made, while an individual is standing between the longitudinal axis of the lower lumbar spine A and the longitudinal axis of the femorae B. Yet, the controlled rigidity of the foam or fibrous material is also sufficently compressible to prevent an individual's abdonimal area and bladder region from receiving substantial compressive force from the support device. The preferred closed cell foam can meet these controlled rigidity criteria. Closed cell foam which can compress approximately 30-40% is preferred. Injecting the closed cell foam into the support device housing is one contemplated method of manufacturing the support device to meet the angular design criteria of the support device. The enlongated apertures 26 and 28 in the support device also help the support device compress under an individual's weight.

When the support device contacts the bones of the points of the hips or the sacrum, the suppot device begins to compress. The upwardly angled support device, which preferably compresses 30-40%, eventually becomes rigid enough to overcome the downward force of the rigid bones to push the bones upward. This results in the longitudinal axes of the femorae B and the lower lumbar spine A each rotating approximately 20°-30° downward relative to the uplifted sacrum area or approximately 40°-60° relative to each other.

When the support device of FIGS. 9 and 10 contacts portions of the abdominal area and bladder region, the support device begins to compress. In contrast to rigid bones, however, the bladder and abominal area organs are able to recede slightly in the body. Upon contact with the support device, therefore, the bladder region and abdominal area organs compress the support device and recede slightly inward themselves so that the support device is not applying a substantial pressure against the abdominal area or the bladder region.

In addition, overlapping slits 142 and 144 are provided on the lower surface 140 of the support device of FIGS. 9 and 10. With these slits or the like, the inner foam or fibrous materials can be added or removed if a doctor or even an individual wants to adjust the angular relationship of the support device upper surface portions 131 and 132 to each other or adjust the angular relationship of any of the upper surfaces to the lower surface 140.

The structure to releasably secure the support device to an individual can be modified in may ways, in addition to retaining straps 50 and 60 with VELCRO pieces 52, 54, 62 and 64, so long as the device can be secured against a resting surface under an individual in a prone positon. The straps could be intergral with the vinyl coated support device. The straps could connect to the upper surface of the support device. There could be one strap across the support device instead of two. Rather than straps even a harness or a shirt could be used. For attachment, VELCRO could be replaced with a belt buckle, buttons or any other conventional releasable attachment structure.

Having described a preferred embodiment in detail, it will be recognized that the foregoing is considered as illustrative only of the principles of the invention. Further, since numerous modifications and changes will readily occur to those skilled in the art, it is not desired to limit the invention to the exact construction, materials, assembly, etc. shown and described. Accordingly, all suitable modifications and equivalents are included within the spirt and scope of the claims appended hereto.

What is claimed is:

1. An orthopedic appliance for changing the angular relationship of an individual's longitudinal axis of the lower lumbar spine to a longitudinal axis of the femorae comprising a support device including:

a first pair of opposite edges which extend substantially parallel to a user's spine and a second pair of opposite edges which extend substantially perpendicular to a user's spine;

a lower suface to be disposed along a resting surface; and an upper surface, disposed above the lower surface, including first and second surface portions angularly disposed relative to one another;

said upper surface being concave when said appliance is viewed from a direction perpendicular to said second pair of opposite edges and said upper surface being convex at its central cross section when viewed from a direction perpendicular to said first pair of opposite edges.

2. A orthopedic appliance as in claim 1, wherein the angle between the first and second upper suface portions results in the prone position angle between the longitudinal axis of the lower lumbar spine and the longitudinal axis of the femorae of an individual being between 120° and 140° as measured about the support device side of each of the longitudinal axes of the lower lumbar spine and the femorae.

3. An orthopedic appliance as in claim 1, wherein the angle between the first and second upper surface portions reuslts in the prone position angle between the longitudinal axis of the lower lumbar spine and the longitudinal axis of the femorae being approximately 130° as measured about the support device side of each of the longitudinal axes of the lower lumbar spine and the femorae.

4. An orthopedic appliance comprising a support device having a first pair of opposite edges which extend substantially parallel to a user's spine and a second pair of opposite edges which extend substantially perpendicular to a user's spine, and having a longitudinal axis along which an individual would lay in a prone position including:
a lower surface to be disposed along a resting surface; and
an upper surface disposed above the lower surface, including first and second surface portions disposed relative to one another at an angle along a longitudinal axis of the support device which substantially equals the angle made, while an individual is standing, between a longitudinal axis of the lower lumbar spine and a longitudinal axis of the femorae of an individual said upper surface being concave when said appliance is viewed from a direction perpendicular to said second pair of opposite edges and said upper surface being convex at its central cross section when viewed from a direction perpendicular to said first pair of opposite edges.

5. An orthopedic appliance as in claim 4, wherein said angle between the first and second upper surface portions ranges approximately between 120° and 140° as measured about an interior angle of the support device upper surface so that when an individual is in a prone position and disposed against the upper surface of the support device, the angle between the longitudinal axis of the lower lumbar spine and the longitudinal axis of the femorae of an individual, as measured about an angle facing the support device upper surface, will range approximately between 120° and 140°.

6. An orthopedic appliance as in claim 5, wherein the support device lower surface is substantially planar and is opposite the angled upper surface, and planes extending from each of the first and second upper surface portions intersect a plane extending from the substantially planar lower surface at substantially equal angles.

7. An orthopedic appliance as in claim 4, wherein said angle between the first and second upper surface portions is approximately 130° as measured about an interior angle of the support device upper surface so that when a individual is in a prone positon and disposed against the upper surface of the support device, the angle between the longitudinal axis of the lower lumbar spine and the longitudinal axis of the femorae of an individual, as measured about an angle facing the support device upper surface, will be approximately 130°.

8. An orthopedic appliance as in claim 4, wherein the support device further comprises a housing and compressible foam-like material disposed within the housing.

9. An orthopedic appliance as in claim 8, wherein, when an individual is in a prone position against the support device along a longitudinal axis of the support device, the foam-like material is sufficiently rigid for the first and second upper surface portions to be at said angle and yet is sufficiently compressible to prevent an individual's abdominal area and bladder region from receiving substantial pressure.

10. An orthopedic appliance as in claim 9, wherein the foam-like material is closed cell foam.

11. An orthopedic appliance as in claim 10, wherein the closed cell foam in the support device can compress approximately 30–40% when an individul is in a prone position against the upper surface of the support device along a longitudinal axis of the support device.

12. An orthopedic appliance as in claim 8, wherein the support device housing further comprises means for adding or removing the compressible foam-like material to or from within the housing.

13. An orthopedic appliance as in claim 4, wherein the support device further comprises:
means, centered along one of said second pair of opposite edges, for defining an aperture on the support device to prevent an individual's abdominal area from receiving substantial pressure when an individual is in a prone position against the support device along a longitudinal axis of the support device; and
means, centered along the other of said second pair of opposite edges, for defining an aperture on the support device to prevent an individual's bladder region from receiving substantial pressure when an individual is in a prone position against the support device along a longitudinal axis of the support device.

14. An orthopedic appliance as in claim 13, wherein each of the abdominal area and the bladder region substantial pressure preventing means further comprise a substantially semi-circular inwardly directed side surface portion centered about a longitudinal axis of the support device.

15. An orthopedic appliance as in claim 14, wherein the distance along the longitudinal axis between the semi-circular side surface portions of the substantial pressure preventing means is approximately three inches.

16. An orthopedic appliance as in claim 4, wherein said concave protion of said upper surface can relieve a front side of an individual between points of an individual's hips from substantial pressure from the support device.

17. An orthopedic appliance comprising:
compressible foam-like material;
a support device having a longitudinal axis along which an individual would lay in a prone position including a housing disposed around the compressible foam-like material, the housing having:
first and second side surfaces which extend approximately parallel to a longitudinal axis of the support device;
third and fourth side surfaces which extend approximately perpendicular to a longitudinal axis of the support device;
a lower surface to be disposed along a resting surface; and an upper surface against which an individual would lay in a prone position along a longitudinal axis of the support device having a centered portion near a center point of a longitudinal axis of the support device and having a plurality of upper surface portions each of which lie in a separate plane, each upper surface portion plane extends downward from the center portion of the upper surface of the support device in an opposite direction from the center portion of the upper surface and along a longitudinal axis of the support device, each of the pair of planes are disposed at an angle of approximately 25° to a plane extending from the lower surface, and the pair of upper surface planes intersect each other at a point approximately near the center portion of the upper surface at an interior facing angle of the support device of approximately 130°; and means for releasably securing the support device on an individual.

18. An orthopedic appliance as in claim 17, wherein the foam-like material comprises closed-cell foam which, when an individual is in a prone position against the support device along a longitudinal axis of the support device, can compress approximately 30-40% to provide sufficient rigidity for the pair of upper surface planes to intersect each other at an interior facing angle of approximately 130° and yet provide sufficient compressibility to prevent an individual's abdominal area and bladder region from receiving substantial pressure.

19. An orthopedic appliance as in claim 18, wherein the closed cell foam compresses uniformaly across its upper suface so that the support device has an angle of approximately 130° between the planes of the upper surface portions and approximately 25° between each of these upper suface portion planes and the lower surface plane when the support device is not beign used by an individual.

20. An orthopedic appliance as in claim 17, wherein the upper surface center point along a longitudinal axis of the support device forms an apex of the support device and defines a common point of an interior angle of the support device of approximately 130°.

21. An orthopedic appliance as in claim 17, wherein the third and fourth side surfaces extending approximately perpendicular to a longitudinal axis of the support device are longer in length than the first and second surfaces.

22. A method for changing the angular relationship of an individual's longitudinal axis of the lower lumbar spine to a longitudinal axis of the femorae when an individual is lying in a face down prone position comprising the steps of:

providing a support device having a lower surface, an upper surface, a first pair of edges which extend substantially parallel to a user's spine and a second pair of edges which extend substantially perpendicular to a user's spine, providing a concave configuration to said upper surface when viewed from a direction perpendicular to said second pair of edges, providing a convex central cross section to said upper surface when viewed from a direction perpendicular to said first pair of edges;

placing said support device lower surface on a resting surface;

positioning said upper surface of the support device against a front portion of an individual, the upper surface having first and second surface portions angularly disposed relative to one another;

applying the first upper suface portion against a front portion of an individual near the lumbar spine of an individual; and applying the second upper surface portion against a front portion of an individual approimately near the femorae of an individual, so that the angular relationship between the applied first and second surface portions recreates in an individual an angle between the longitudinal axis of the lower lumbar spine and the longitudinal axis of the femorae which is approximately equal to the angular relationship between these longitudinal axes while an individual is standing.

23. The method of claim 22, wherein the first and second upper surface portion applying steps result in the prone position recreated angle between the longitudinal axis of the lower lumbar spine and the longitudinal axis of the femorae of an individual to range approximately between 120° and 140° as measured about the support device side of each of the longitudinal axes of the lumber spine and the femorae.

24. The method of claim 22, wherein the first and second upper surface applying steps result in the prone position angle between the longitudinal axis of the lower lumbar spine and the longitudinal axis of the femorae of an individual to equal approximately 130° as measured about the support device side of each of the longitudinal axes of the lumbar spine and the fomorae.

25. The method of claim 22, further comprising the step of releasably securing the support device on an individual.

26. The method of claim 22, wherein said applying step is effected by the weight of the individual resting on said first and second upper surface portions.

27. The method of claim 23, wherein said applying step is effected by the weight of the individual resting on said first and second upper surface portions.

28. The method of claim 24, wherein said applying step is effected by the weight of the individual resting on said first and second upper surface portions.

29. The method of claim 25, wherein said applying step is effected by the weight of the individual resting on said first and second upper surface portions.

* * * * *